(12) United States Patent
Schuler-Maloney et al.

(10) Patent No.: US 6,238,907 B1
(45) Date of Patent: May 29, 2001

(54) CONTAINER FOR STORING AND EXAMINING PLACENTAS

(75) Inventors: Doris Schuler-Maloney, 1661 60$^{th}$ Ave., St. Charles, IA (US) 50240; Harrison W. Pratt, II, Des Moines, IA (US)

(73) Assignee: Doris Schuler-Maloney, St. Charles, IA (US)

( * ) Notice: Subject to any disclaimer, the term of this patent is extended or adjusted under 35 U.S.C. 154(b) by 0 days.

(21) Appl. No.: 09/257,924

(22) Filed: Feb. 26, 1999

(51) Int. Cl.$^7$ .................................................... C12M 3/00
(52) U.S. Cl. .................................... 435/284.1; 435/288.3; 435/305.1; 435/305.4; 33/1 BB; 33/522; 206/459.5; 604/318; 604/404; 73/426; 73/427
(58) Field of Search ..................... 435/40.5, 1.1, 435/284.1, 288.1, 288.3, 304.1, 305.1, 305.4, 307.1; 206/305, 459.5; 422/102; 356/246; 604/404, 318; 359/397; 73/427, 426; 33/522, 712, 1 V, 1 BB

(56) References Cited

U.S. PATENT DOCUMENTS

| | | |
|---|---|---|
| 226,392 * | 4/1880 | Felbel . |
| 1,052,464 * | 2/1913 | Criswell . |
| 2,252,503 | 8/1941 | Griffin . |
| 2,340,369 * | 2/1944 | Downer . |
| 3,244,169 | 4/1966 | Baxter . |
| 3,575,225 | 4/1971 | Muheim . |
| 3,791,524 | 2/1974 | Cho . |
| 3,810,367 | 5/1974 | Peterson . |
| 4,221,295 | 9/1980 | Tuchband et al. . |
| 4,268,967 * | 5/1981 | Brana et al. . |
| 4,334,361 * | 6/1982 | Gorski et al. . |
| 4,454,210 * | 6/1984 | Ariyama et al. . |
| 4,474,016 | 10/1984 | Winchell ................................ 62/60 |
| 4,681,839 | 7/1987 | Swartz . |
| 4,784,656 | 11/1988 | Christian . |
| 4,925,047 | 5/1990 | Valentine et al. . |
| 5,004,681 | 4/1991 | Boyse et al. . |
| 5,383,472 | 1/1995 | Devlin et al. ....................... 128/771 |
| 5,422,076 | 6/1995 | Jones . |
| 5,640,969 | 6/1997 | Davis . |
| 5,674,227 * | 10/1997 | Burns . |
| 5,841,541 * | 11/1998 | Dlugos . |
| 6,138,371 * | 10/2000 | Lippa et al. . |

FOREIGN PATENT DOCUMENTS 1239379   7/1988   (CA) ....................... 81/18

* cited by examiner

Primary Examiner—William H. Beisner
(74) Attorney, Agent, or Firm—Zarley, McKee, Thomte, Voorhees & Sease

(57) ABSTRACT

A container for examination and storage of a placenta includes a bottom wall, at least one substantially upright side wall joined to the bottom wall to define an interior and an open top. The side walls and/or the bottom wall have indicia thereon adapted to measure the size of the placenta in three dimensions. Indicia are also provided to measure the umbilical cord. The container is stackable for storage, and labeling areas are provided. A basic method of examining a placenta is disclosed, along with further steps and variations.

14 Claims, 3 Drawing Sheets

CONTAINER FOR STORING AND EXAMINING PLACENTAS

BACKGROUND OF THE INVENTION

The present invention relates to the field of medical science and the sub-field of obstetrics. More particularly, this invention relates to a container for storing and examining a placenta following the delivery of a baby. The invention provides a gross placenta examination kit (GPEK) and a method for using the same for non-surgical evaluation of the placenta.

In general, sterile specimen containers for body tissue and the like are well known. One such container is disclosed by Muheim in U.S. Pat. No. 3,575,225. A pliable or flexible plastic bag attaches to a rigid spatula-like frame with a lid pivotally mounted thereon and has a top opening for insertion of a placenta, other medical items, and even food. A 2000 cc transparent or translucent bag is recommended for collection and disposal of a placenta. The bag has a single set of markings calibrated for measuring the fluid volume of the placenta in a constrained state within the flexible bag. The markings are disposed only on one side wall of the bag. No suggestion is made that the marks should protrude from the surface of the bag.

There is a need for a container for examining and storing the placenta in essentially a free state, wherein the placenta is supported on its maternal surface and is in an open, easily visible and accessible condition conducive to examination. There is also a need for a container which can measure free state length, width, and height or thickness of a placenta, as well as the diameter and length of the umbilical cord if present.

Therefore, a primary objective of the present invention is the provision of an improved container for gross examination and storage of a placenta.

Another objective of this invention is the provision of a method of examining a placenta on a gross basis for various characteristics or abnormalities.

Another objective of this invention is the provision of a container which is economical to produce and yet easy, accurate and reliable in use.

These and other objectives will become apparent from the drawings, as well as the description and claims which follow.

SUMMARY OF THE INVENTION

The present invention relates to a method and container for examining and storing placentas. The plastic container has a bottom with one or more upright side walls joined thereto. The bottom receives and supports a placenta which can have a length of umbilical cord attached. The side walls include a multitude of visually discernible marks thereon arranged along at least three different orthogonal axes. The marks are preferably formed as ridges or protrusions on the inside of the respective side walls, although other forms of marking will suffice.

A first set of marks includes marks spaced horizontally at known intervals along one of the bottom wall or the side walls so as to measure the length of the placenta, a second set of marks includes marks spaced horizontally along the bottom or one of the other side walls perpendicular to the first set of marks so as to measure the width of the placenta. A third set of marks includes marks spaced apart and extending upwardly at known intervals along one of the side walls so as to measure the height or thickness of the placenta from the bottom wall. The third set of marks extends perpendicular to the first and second set of marks.

A fourth set of marks spaced apart at known intervals can also be provided on the bottom wall or one of the side walls so as to measure the diameter of the umbilical cord.

The container is constructed so as to be stackable. A lid can be sealingly mounted to the top of the side walls in order to cover the container. The placenta specimen can be placed in the container, then sealed and stacked on a refrigerator shelf for storage. When the desired retention period expires, the placenta specimen can be discarded as biohazard waste, preferably in the same container.

DETAILED DESCRIPTION OF THE PREFERRED EMBODIMENT

Figure 1:
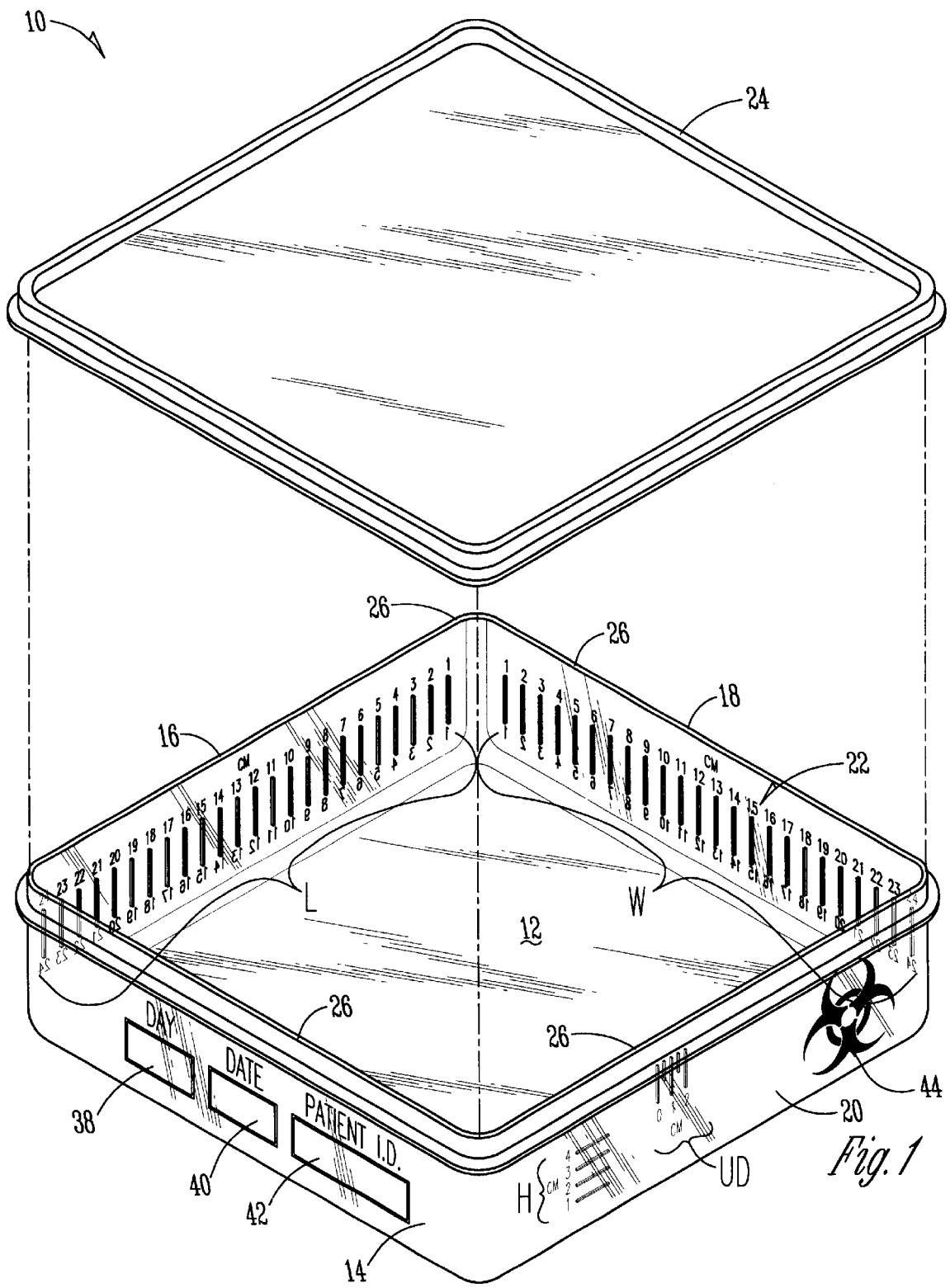
FIG. 1 is an exploded perspective view of the container of this invention.

In the drawings and the description which follow, the container of this invention is generally designated by the reference numeral 10. FIG. 1 shows that the container 10 has a bottom wall 12 which is joined to a plurality of interconnected, substantially upright side walls 14, 16, 18 and 20. Preferably four side walls are provided so that the container has a substantially rectangular shape. However, other shapes are contemplated and will suffice, even a continuous side wall forming a round or oval shape. The side wall(s) extend upwardly from the bottom wall 12 to define an open top 22 therebetween. An optional lid 24 can cover the open top 22. When a lid 24 is provided, a lip 26 extends around the open top 22 so as to allow the lid 24 to sealingly mount on the top of the side walls 14, 16, 18, 20 of the container 10.

The container 10, including the lid 24, are molded or otherwise formed from a plastic material that is slightly pliable. However, the material must be sufficiently rigid to support the placenta 28 horizontal without significant deflection. The material is impervious to fluids. The plastic material is translucent, or more preferably transparent (clear), but opaque material will also suffice if the indicia discussed below are clearly discernible from the inside of the container 10. In the preferred embodiment, the container 10 is unsterilized and intended to be disposable, but sterilization and/or reuse are also viable options. Furthermore, sterile drapes can be used to handle the placenta 28 if infection is suspected.

On one side of the container 10, for example on side wall 16, spaced apart visually discernable indicia L are included therealong for measuring the length of a placenta 28. The indicia L include a set of equally spaced vertical marks, lines or ridges which are numbered for ease of measuring using the scale or system of units desired. The numbers can be arranged to be readable from the inside of the container 10 only, from outside of the container 10 only, or from both the inside and outside of the container 10 as shown. The marks originate from one of the inside corners of the container 10. Similar indicia W is provided along the second side wall 18. This second set of marks also originates from the corner between side walls 16 and 18. The marks on side wall 18 extend perpendicular to the marks on the side wall 16. Thus, one of the side walls 16, 18 can be used to measure the length of the placenta 28, and the other of the side walls 18, 16 can be used to measure the width of the placenta 28.

The third side wall 20 includes two sets of visually discernable indicia H, UD thereon. The first set of indicia H on side wall 20 and the third set overall is a set of marks including short horizontal equally spaced apart lines positioned above the bottom wall 12 of the container 10. Corresponding numbers are provided adjacent to the marks to show the distance from the bottom wall 12. These marks are used to determine the height or thickness of the placenta when it rests on the bottom wall 12. Thus, the length, width and height of the placenta can be quickly and accurately determined using the three sets of indicia described above. Note that the product of the length, width and height does not equal the fluid volume, which the placenta would occupy. The information provided by these individual length, width, and height or thickness measurements potentially highlights any abnormalities, which might exist in the placenta 28.

Figure 2:
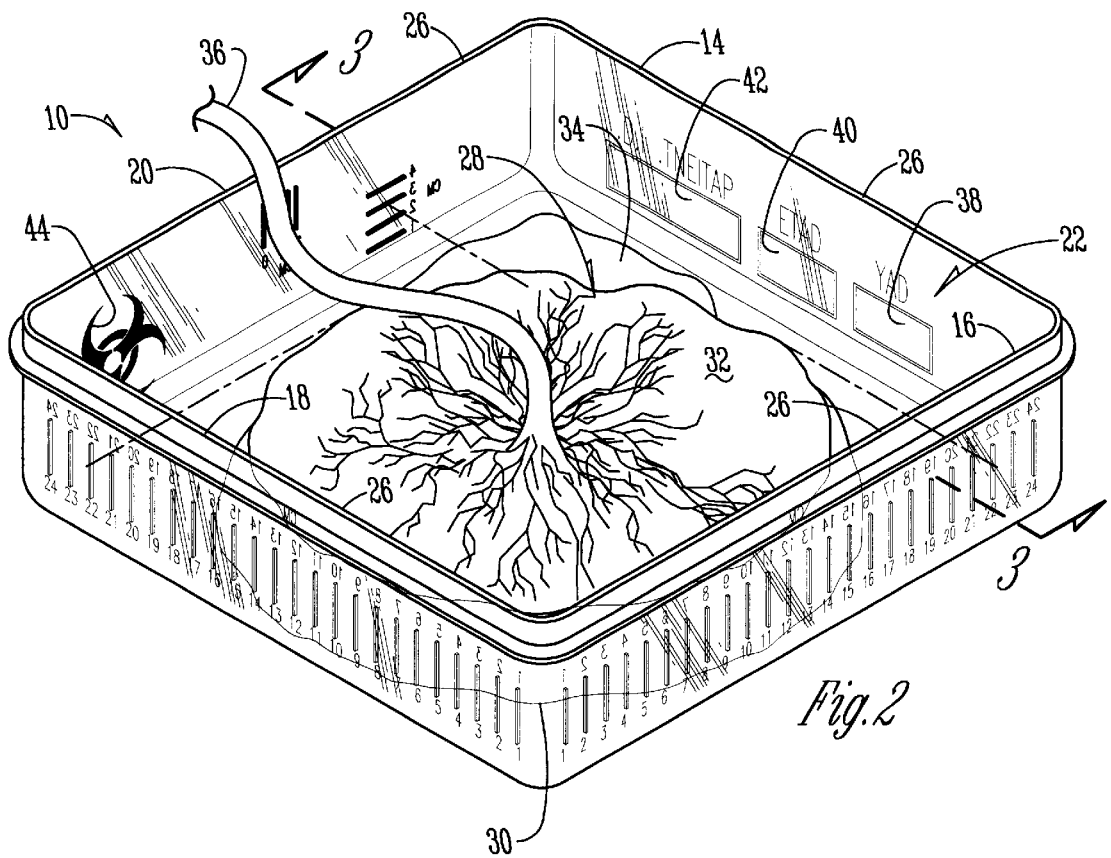
FIG. 2 is a perspective view of the container of FIG. 1 with the lid removed and a placenta placed therein for gross examination and storage.

As best seen in FIG. 2, the placenta 28 has a maternal surface 30 which rests on the bottom wall 12 of the container 10 and a fetal surface 32 which is directed toward the open top 22 of the container 10. A membrane 34 and an elongated umbilical cord 36 are connected to the fetal surface 32. The indicia UD on the side wall 20 includes a set of equally spaced vertical lines and at least some numbers corresponding thereto, which indicate the diameter of the umbilical cord 36. The side wall 20 of the container 10 also includes a bio-hazard warning symbol molded, marked or affixed thereon.

Since the use of the metric or international system of units is prevalent in the medical field, the indicia L, W, H, UD and associated numbers are preferably in centimeters (cm) or subdivisions or multiples thereof. The container 10 is preferably large enough to accommodate indicia as follows: L=24 cm; W=24 cm; H=4 cm; and UD=2 cm. Preferably the inside of the container 10 itself is approximately 25 cm long, 25 cm wide, and 6 cm high. Markings reminding the use of the scale or system of units are also recommended.

Figure 3:
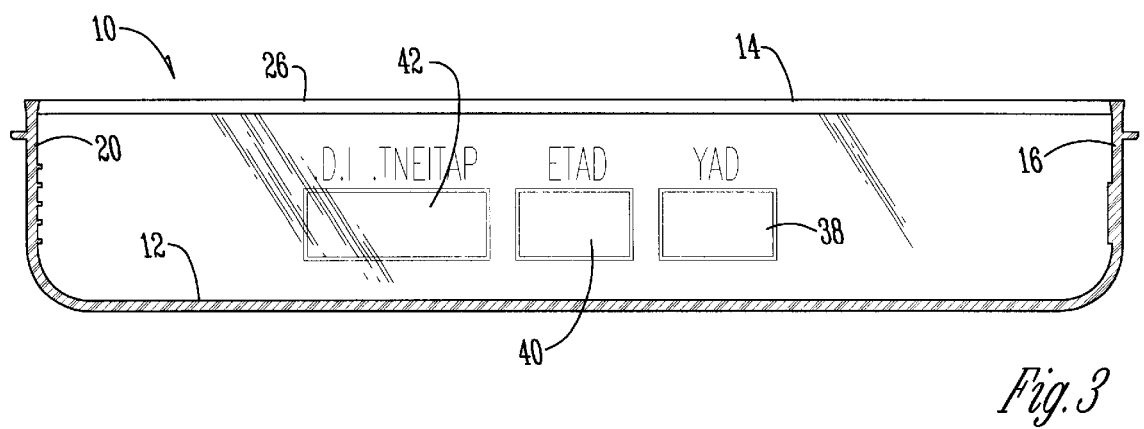
FIG. 3 is a sectional view of the container taken along line 3—3 in FIG. 2.

As best seen in FIG. 3, the indicia L, W, H protrude slightly from their respective walls in the preferred embodiment. Here the indicia L, W, and H protrude into the interior of the container 10 to allow them to be viewed with the lid 24 removed, but they could also or alternatively protrude outside the container 10. Protrusions of approximately 1–5 mm, more preferably about 2 mm, are readily visible. Indicia UD can also protrude if desired.

Because the density of the material used to form the container 10 is known and can be controlled closely through conventional production molding processes, the mass of the container 10 is basically known. Even if there is significant variation, the container 10 can be weighed before use. Then the mass of the placenta 28 can be obtained by weighing the full container and subtracting the mass of the empty container.

The side wall 14 has three areas 38, 40, 42 thereon for labeling the container 10 with the day of the week, date, and patient identification information corresponding to the placenta 28 stored therein. Adhesive labels can be utilized or, more preferably, the outer surface of the plastic container 10 can be left slightly rough in the label areas 38, 40, 42 so that a grease pencil or conventional ballpoint ink pen can be utilized to record the necessary information.

The side walls 14, 16, 18, 20 of the container 10 are inclined outwardly slightly so that another container 10 can be stacked on top thereof. With or without outwardly inclined side walls, the container 10 is stackable upon itself when the lid 24 is installed. See FIG. 4.

Following the delivery or removal of the placenta 28 from the mother's body, the gross placental examination kit (GPEK) 10 provides the following method or methods of examination and storage. A health care professional, typically a nurse, grabs a container 10 and weighs it if the weight of the empty container 10 is not known with sufficient accuracy. The nurse then positions the container 10 so as to receive the placenta 28. The nurse places the placenta 28 in the container or GPEK 10. The placenta 28 sits in the GPEK 10 while the nurse finishes other tasks. During this time, blood from many of the blood vessels in the placenta 28 will drain into the container 10. Then, while carefully holding the placenta 28 in the container 10, the nurse tips the container 10 over a sink to drain off the excess fluids. Then the nurse orients the placenta 28 in the container 10 with the maternal side 30 resting on the bottom wall 12 and the fetal side 32 facing up. In this position the membrane 34 and umbilical cord 36 can also be examined easily. The net weight or mass of the placenta 28 is documented by weighing the full container 10 and subtracting the weight or mass of the empty container 10. Elevating the opposite corner of the container 10 causes the placenta 28 or placental disk to slide into the corner of the container 10 which exists between the origins of the indicia L, W. Using the indicia L, W, the nurse determines the length and width of the placenta 28 respectively and documents the results. Sliding or otherwise moving the placenta 28 to the opposite corner allows the nurse to determine the height or thickness of the placenta 28 using indicia H. The maximum, minimum or average height can be roughly approximated.

Pulling the umbilical cord 36 in front of the indicia UD enables the nurse to determine its uniformity and diameter, which are then recorded with the rest of the nurse's observations, if desired. The length of the umbilical cord can also be determined by extending it alongside (adjacent and parallel to) the walls 16, 18. Some simple arithmetic may be necessary. Color and knots can be documented. The number of umbilical cord blood vessels and their integrity can be determined, as well as the umbilical cord insertion on the fetal surface 32. Other characteristics of the placenta 28 can be determined and documented while the placenta 28 is in the container 10, including overall shape, type of presentation, overall integrity, abnormalities in color, and smoothness and blemishes. For example, the fetal surface 32 is examined for color, smoothness, and blood vessel integrity. Any extraplacental membranes 34, which are still attached to the placenta 28, can be examined too. The nurse palpates the parenchyma (placental disk) to determine and document its consistency.

Before or after the fetal surface 32 is examined, the nurse can orient the placenta 28 in the container 10 so that the material surface 30 is facing up and can be examined for intactness and attached blood clots. It is also possible to take some or all of the L, W, and H measurements with the maternal surface 30 of the placenta 28 facing up, as long as it is substantially flat. A consistent procedure should be utilized for best results.

The nurse snaps the lid 24 onto the container 10 if the specimen is to be stored after the examination. Copies of the form containing the results of the examination can be distributed to other medical personnel as needed. Labeling the container 10 with the appropriate information in label areas 38, 40, 42 ensures that the specimen is properly identified and therefore retrievable.

In some cases the specimen is sent to a pathology lab for further study. A full thickness strip of placenta and membranes and two pieces of the umbilical cord can be placed in a small container with a preservative, such as formalin, therein and sent to a pathology lab for histologic study. Later, these tissue samples are sectioned, studied, documented and embedded in a block of paraffin which can be retained for 21 years in case of possible birth defect litigation.

Figure 4:
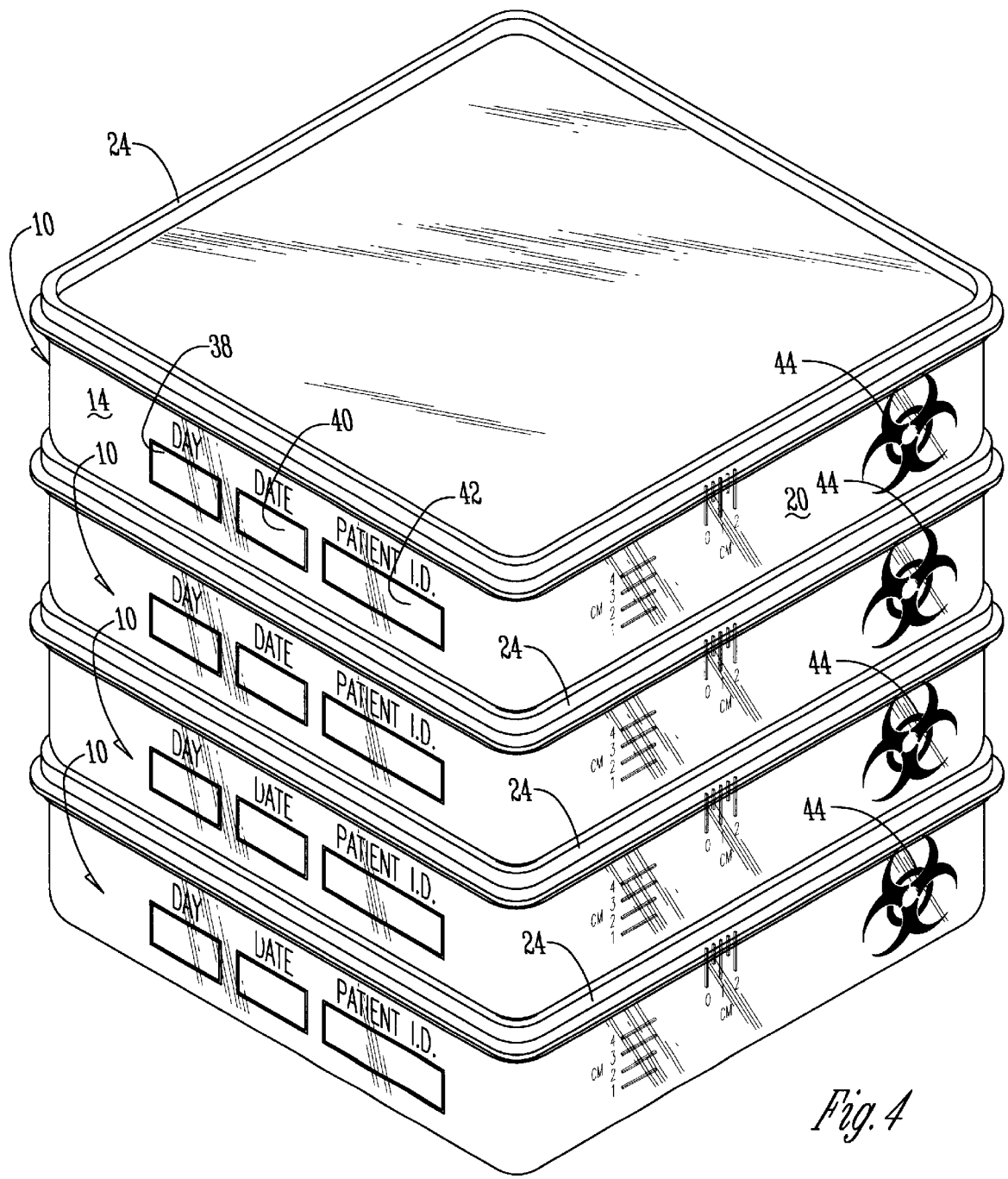
FIG. 4 is a perspective view of several of the sealed containers of FIG. 1 stacked on top of each other.

The containers 10 are typically stacked as in FIG. 4 and placed in a refrigerator for a limited period of time in case further examination, pathology, sectioning or other testing is required. After a predetermined time, such as seven days, the container 10 and the specimen stored therein are disposed of in an appropriate biohazard waste receptacle. The seven day disposal cycle would be particularly advantageous when the refrigerator is divided into seven compartments or shelves, one for each day of the week. After one week, the week-old specimens could be discarded and specimens from the current day could be stored in that space. The biohazard symbol 44 reminds the user of the need for proper disposal.

As the above discussion suggests, the container 10 is quite versatile. For instance, it is contemplated that the indicia L, W could be located on the bottom wall 12 of the container 10 rather than on the side(s) 16, 18 of the container 10. Thus, it can be seen that the present invention at least achieves its stated objectives.

In the drawings and specification there has been set forth a preferred embodiment of the invention, and although specific terms are employed, these are used in a generic and descriptive sense only and not for purposes of limitation. Changes in the form and the proportion of parts as well as in the substitution of equivalents are contemplated as circumstances may suggest or render expedient without departing from the spirit or scope of the invention.

What is claimed is:

1. A container for examination and storage of a placenta having a length, width, and height, comprising:
a bottom wall;
a plurality of upright side walls that are joined to each other and to the bottom wall so as to define a top opening surrounded by a top rim;
the side walls and the bottom wall being formed of a substantially clear molded plastic material so as to permit visual examination of the placenta while the placenta is in the container; and
at least three sets of spaced apart visually discernible measuring indicia imprinted on the container and arranged so as to measure the size of a placenta in at least three dimensions.

2. A container for examination and storage of a placenta having a length, width, and height, comprising:
a bottom wall;
a plurality of upright side walls that are joined to each other and to the bottom wall so as to define a top opening surrounded by a top rim;
a lid mounted in sealing contact and engagement with the top rim so as to seal the placenta and any fluid associated therewith inside the container;
the lid, the side walls, and the bottom wall being formed of a substantially clear molded plastic material so as to permit visual examination of the placenta in the container without removing the lid; and
at least three sets of spaced apart visually discernible measuring indicia imprinted on the container and arranged so as to measure the size of a placenta in at least three dimensions.

3. The container of claim 2 wherein the plurality of side walls includes a first side wall that has horizontally spaced vertical disposed indicia therealong which are adapted to measure the length of the placenta.

4. The container of claim 3 wherein the plurality of side walls includes a second side wall that has horizontally spaced vertical disposed indicia therealong which are adapted to measure the width of the placenta, the indicia on the second side wall extending perpendicular to the indicia on the first side wall.

5. The container of claim 4 wherein the plurality of side walls includes a third side wall that has vertically spaced horizontally disposed indicia spaced thereupon which are adapted to measure the height of the placenta, the indicia on the third side wall extending perpendicular to the indicia on the first and second side walls.

6. The container of claim 2 wherein the bottom wall, the lid, and the side walls are substantially rigid.

7. The container of claim 2 wherein the indicia are a plurality of spaced apart lines on the inside of the container.

8. The container of claim 2 wherein the indicia are a plurality of spaced apart ridges protruding into the inside of the container.

9. The container of claim 2 wherein the indicia are equally spaced apart.

10. The container of claim 2 wherein the lid of the container has a recess therein and the bottom wall of one container can be fitted into the recess so as stack one sealed container securely on top of another sealed container.

11. The container of claim 2 wherein an area is provided on one of the side walls to place a label thereon for identifying the placenta disposed in the container.

12. The container of claim 2 wherein the container is disposable.

13. The container of claim 2 wherein one of the side walls includes a set of spaced apart indicia adapted to measure the diameter of an umbilical cord.

14. The container of claim 2 wherein the lid frictionally seals on the top rim of the side walls.

* * * * *